(12) United States Patent
Linderman

(10) Patent No.: US 8,771,276 B2
(45) Date of Patent: Jul. 8, 2014

(54) SYSTEMS AND METHODS FOR FORMING A CAVITY IN, AND DELIVERING CURABLE MATERIAL INTO, BONE

(75) Inventor: Evan D. Linderman, Northbrook, IL (US)

(73) Assignee: CareFusion 2200, Inc., San Diego, CA (US)

( * ) Notice: Subject to any disclaimer, the term of this patent is extended or adjusted under 35 U.S.C. 154(b) by 798 days.

(21) Appl. No.: 12/957,793

(22) Filed: Dec. 1, 2010

(65) Prior Publication Data

US 2012/0143202 A1 Jun. 7, 2012

(51) Int. Cl.
*A61B 17/88* (2006.01)
*A61F 2/46* (2006.01)

(52) U.S. Cl.
USPC ........................... 606/86 R; 606/279

(58) Field of Classification Search
USPC .................... 606/86 R, 279, 92–94
See application file for complete search history.

(56) References Cited

U.S. PATENT DOCUMENTS

| | | | |
|---|---|---|---|
| 4,969,888 A | 11/1990 | Scholten et al. | |
| 5,108,404 A | 4/1992 | Scholten et al. | |
| 5,827,289 A | 10/1998 | Reiley et al. | |
| 5,972,015 A | 10/1999 | Scribner et al. | |
| 6,048,346 A | 4/2000 | Reiley et al. | |
| 6,066,154 A | 5/2000 | Reiley et al. | |
| 6,235,043 B1 | 5/2001 | Reiley et al. | |
| 6,241,734 B1 | 6/2001 | Scribner et al. | |
| 6,248,110 B1 | 6/2001 | Reiley et al. | |
| 6,423,083 B2 | 7/2002 | Reiley et al. | |
| 6,558,390 B2 * | 5/2003 | Cragg ............................ | 606/80 |
| 6,607,544 B1 | 8/2003 | Boucher et al. | |
| 6,623,505 B2 | 9/2003 | Scribner et al. | |
| 6,641,587 B2 | 11/2003 | Scribner et al. | |
| 6,663,647 B2 | 12/2003 | Reiley et al. | |
| 6,719,761 B1 | 4/2004 | Reiley et al. | |
| 6,726,691 B2 | 4/2004 | Osorio et al. | |
| 6,899,719 B2 | 5/2005 | Reiley et al. | |
| 6,923,813 B2 | 8/2005 | Phillips et al. | |
| 6,981,981 B2 | 1/2006 | Reiley et al. | |
| 7,044,954 B2 | 5/2006 | Reiley et al. | |
| 7,153,306 B2 | 12/2006 | Ralph et al. | |
| 7,156,861 B2 | 1/2007 | Scribner et al. | |
| 7,963,967 B1 * | 6/2011 | Woods ............................ | 606/79 |
| 2006/0276819 A1 | 12/2006 | Osorio et al. | |
| 2007/0118142 A1 | 5/2007 | Krueger et al. | |
| 2007/0197971 A1 | 8/2007 | Krueger et al. | |
| 2007/0198024 A1 | 8/2007 | Plishka et al. | |
| 2008/0116224 A1 | 5/2008 | Krueger et al. | |
| 2008/0312637 A1 | 12/2008 | Miller et al. | |
| 2008/0319444 A9 | 12/2008 | Osorio et al. | |
| 2009/0043345 A1 | 2/2009 | Mathews | |

(Continued)

*Primary Examiner* — Anu Ramana
(74) *Attorney, Agent, or Firm* — Brinks Gilson & Lione

(57) ABSTRACT

Methods of injecting curable material within a bone structure, such as vertebroplasty, include locating a distal end of an access cannula within the bone structure. A channel creating device is inserted into a cannula lumen. A distal segment of the channel creating device is distally advanced from cannula distal end and into the bone structure. A curved channel is created in the bone structure with the distally advancing distal segment. A distal portion of a cavity creating device is then inserted into the cannula lumen, with the distal portion including an expandable body carried by an elongated body. The distal portion is distally advanced, following a path of the curved channel. The expandable body is transitioned to the expanded state to form a cavity in the bone structure. Finally, curable material is delivered to the cavity.

16 Claims, 12 Drawing Sheets

(56) References Cited

U.S. PATENT DOCUMENTS

| | | |
|---|---|---|
| 2010/0087828 A1 | 4/2010 | Krueger et al. |
| 2010/0100099 A1 | 4/2010 | Reilly et al. |
| 2010/0100184 A1 | 4/2010 | Krueger et al. |
| 2010/0121336 A1 | 5/2010 | Linderman et al. |

* cited by examiner

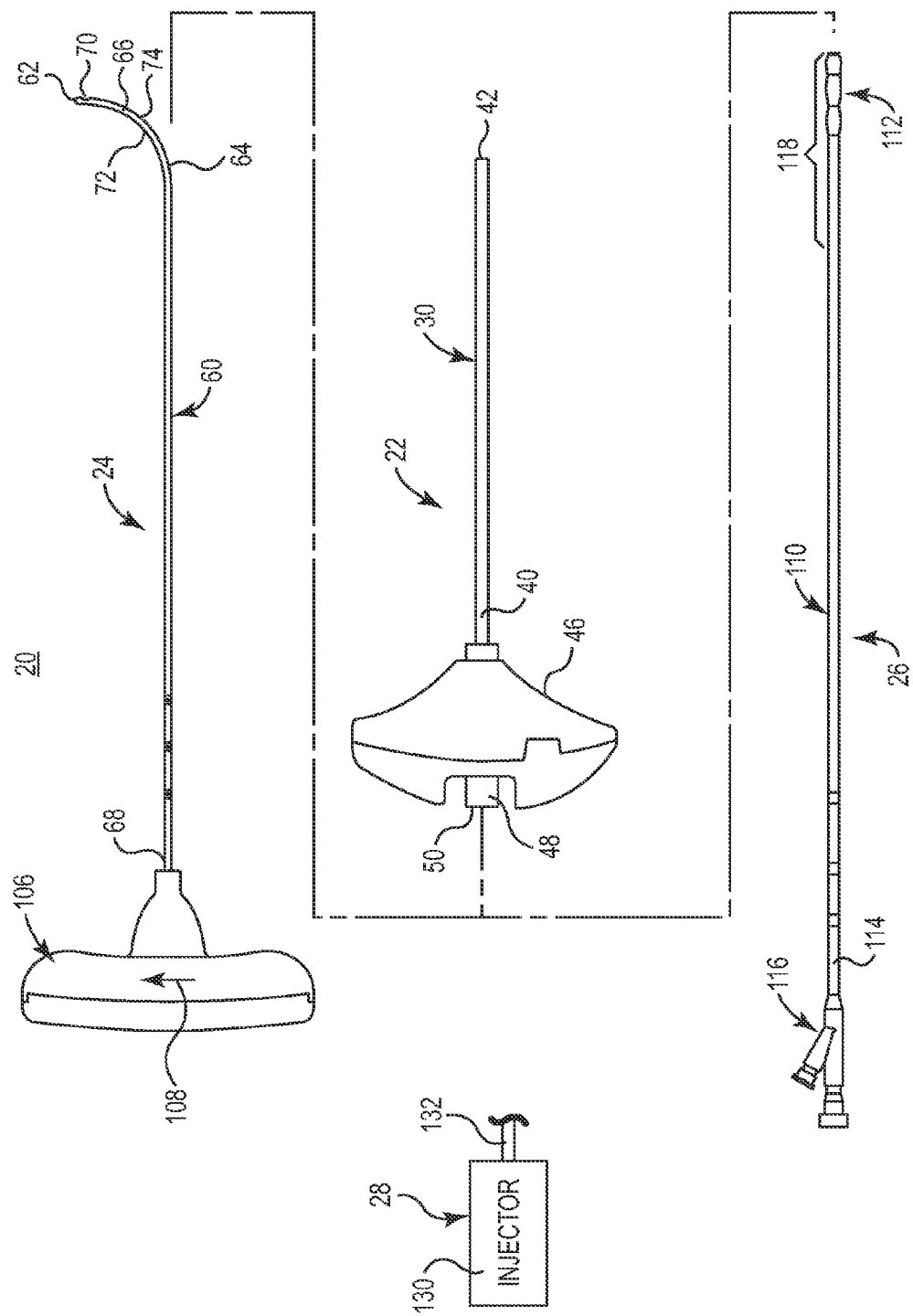

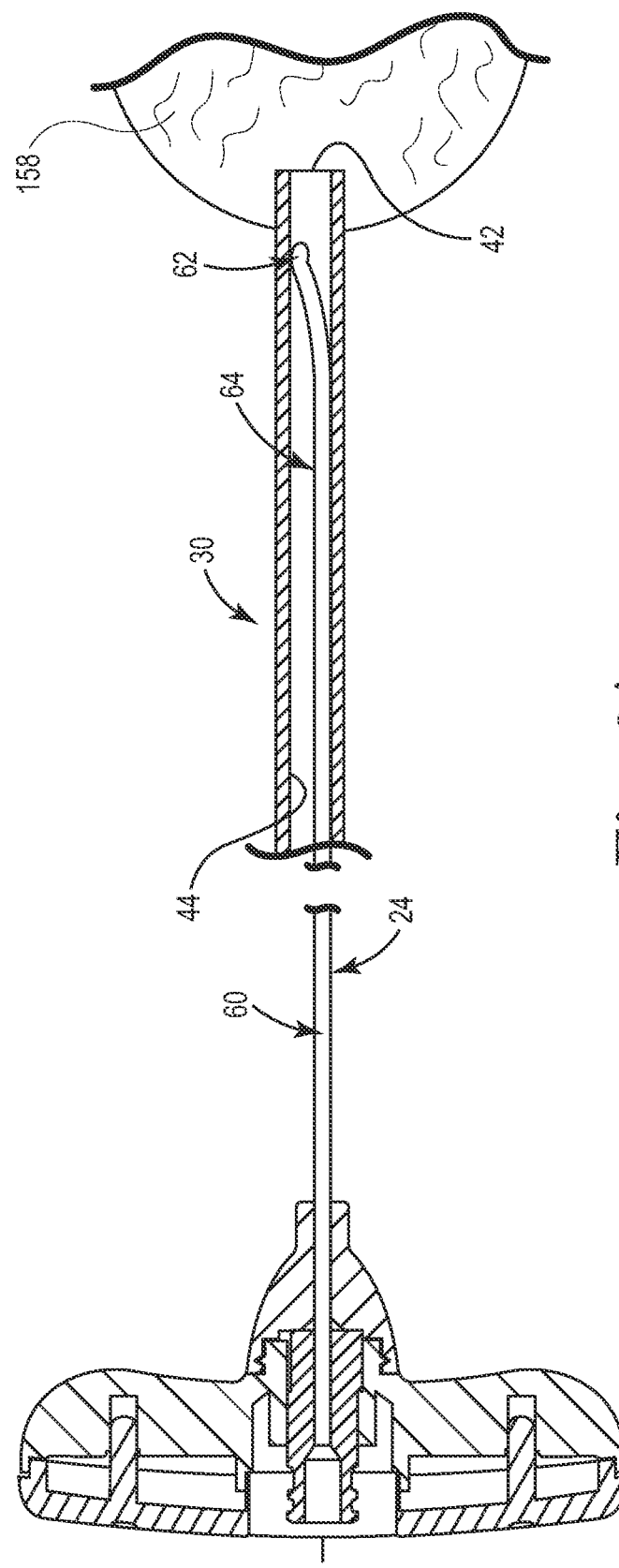

SYSTEMS AND METHODS FOR FORMING A CAVITY IN, AND DELIVERING CURABLE MATERIAL INTO, BONE

BACKGROUND

The present disclosure relates to systems and methods for stabilizing bone structures. More particularly, it relates to systems and methods for forming a cavity inside a bone structure, such as a vertebral body, and delivering a stabilizing material into the cavity.

Surgical intervention at damaged or compromised bone sites has proven highly beneficial for patients, for example patients with back pain associated with vertebral damage.

Bones of the human skeletal system include mineralized tissue that can be generally categorized into two morphological groups: "cortical" bone and "cancellous" bone. Outer walls of all bones are composed of cortical bone, which has a dense, compact bone structure characterized by a microscopic porosity. Cancellous or "trabecular" bone forms the interior structure of bones. Cancellous bone is composed of a lattice of interconnected slender rods and plates known by the term "trabeculae".

During certain bone-related procedures, cancellous bone is supplemented by an injection of a palliative (or curative) material employed to stabilize the trabeculae. For example, superior and inferior vertebrae in the spine can be beneficially stabilized by the injection of an appropriate, curable material (e.g., PMMA or other bone cement or curable material). In other procedures, percutaneous injection of stabilization material into vertebral compression fractures, by, for example, transpedicular or parapedicular approaches, has proven beneficial in relieving pain and stabilizing damaged bone sites. Such techniques are commonly referred to as vertebroplasty. Other skeletal bones (e.g., the femur) can be treated in a similar fashion. Regardless, bone in general, and cancellous bone in particular, can be strengthened and stabilized by palliative insertion or injection of bone-compatible material.

Using vertebroplasty as a non-limiting example, a conventional technique for delivering the bone stabilizing material entails placing an access cannula with an internal stylet into the targeted delivery site (i.e., the vertebral body). The access cannula and stylet are used in conjunction to pierce the cutaneous layers above the hard tissue to be supplemented, then to penetrate the hard cortical bone of the vertebra, and finally to traverse into the softer cancellous bone underlying the cortical bone. Once positioned in the cancellous bone, the stylet is removed, leaving the access cannula in an appropriate, lodged position for delivery of curable material (e.g., via a needle or tube inserted through the access cannula) to the trabecular space of the vertebral body that in turn reinforces and solidifies the target site.

In some instances, an effectiveness of the procedure can be enhanced by forming a cavity or void within the cancellous bone, and then depositing the curable material in the cavity. For example, a balloon or other expandable device can be initially deployed and then expanded. This action, in turn, compresses cancellous bone to form a cavity. To minimize the duration of the procedure and number of tools required, it is desirable to use the same access cannula to first guide delivery of the cavity forming device, and subsequently to guide delivery of the curable material. Stated otherwise, one desirable procedure entails initially locating and lodging a distal end of the access cannula within the bone, immediately adjacent the target site. The cavity forming device is then delivered through the access cannula to the target site and then operated to form the cavity. In this regard, the access cannula is normally a metal tube rigidly defining a central axis. Conventional cavity forming devices typically include a longitudinally linear shaft carrying the expandable body. With this linear configuration, the shaft/expandable body progress from the access cannula into the bone structure along a relatively straight or linear path that is coaxial with the access cannula's central axis. While viable, this linear approach may inhibit the surgeon's ability to form the cavity at a desired location. For example, with vertebroplasty, the confined nature of the inner vertebral body and surrounding anatomy oftentimes necessitates insertion of the access cannula immediately adjacent one of the vertebra's pedicles. This access site, in combination with the linear configuration of the access cannula and expandable body-carrying shaft, dictates that the expandable body can only be located in a relatively limited area in line with the access cannula's central axis. In some instances, this restricted spatial location of the expandable body relative to the desired target site may not be optimal.

In light of the above, a need exists for improved systems and methods for forming a cavity in a compromised bone site, such as a vertebral body, and for delivering stabilizing material to the so-formed cavity.

SUMMARY

Some aspects in accordance with principles of the present disclosure relate to injecting curable material to a delivery site within a bone structure. The method includes locating a distal end of an access cannula within the bone structure. The access cannula forms a lumen and defines a central axis. A channel creating device is inserted into the lumen. A distal segment of the channel creating device is distally advanced from the distal end of the access cannula and into the bone structure. A curved channel is created in the bone structure with the distally advancing distal segment. In this regard, the curved channel defines a curve relative to the central axis. The channel creating device is removed. A distal portion of a cavity creating device is inserted into the access cannula lumen, with the distal portion including an expandable body carried by an elongated body. The expandable body is operable between a contracted state and an expanded state. During insertion into the access cannula, the expandable body is in the contracted state. The distal portion is then distally advanced from the distal end of the access cannula, with the distal portion of the cavity creating device following a path of the curved channel. The expandable body is transitioned to the expanded state to form a cavity in the bone structure. Finally, curable material is delivered to the cavity. In some embodiments, the expandable body is a balloon. In other embodiments, the distal segment of the channel creating device has a shape memory characteristic and naturally assumes a curved shape in longitudinal extension; in related embodiments, the distal segment deflects from the curved shape toward a more straightened shape when disposed within the access cannula, and naturally reverts toward the curved shape when distally extended from the access cannula. In yet other embodiments, the distal segment of the channel creating device includes a shaft terminating at a distal tip, with the distal tip configured to bore through bone structure with distal advancement from the access cannula.

BRIEF DESCRIPTION OF THE DRAWINGS

FIG. 1 is a exploded side view of a system for forming a cavity in, and delivering curable material into, bone in accordance with principles of the present disclosure;

DETAILED DESCRIPTION

Figure 2A:
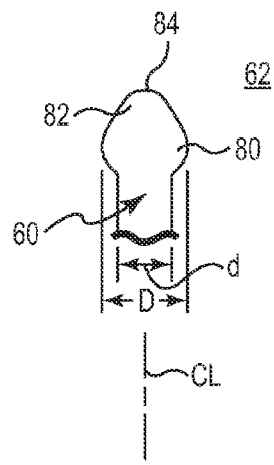
FIG. 2A is an enlarged side view of a distal tip portion of a channel forming device component of the system of FIG. 1.

One embodiment of a curable material delivery system 20 in accordance with principles of the present disclosure is shown in FIG. 1. The system 20 includes an access cannula assembly 22, a channel forming device 24, a cavity forming device 26, and a material delivery device 28. Details on the various components are provided below. In general terms, however, the access cannula assembly 22 includes an access cannula 30 for insertion into a bone site of interest in a patient (e.g., a vertebra). Once the access cannula 30 is desirably located relative to the bone site, a portion of the channel forming device 24 is delivered to the bone site via the access cannula 30, and operated to form a curved channel. The channel forming device 24 is then replaced with the cavity forming device 26, and operated to form a cavity along the curved channel. The material delivery device 28 is then operated to deliver curable material to the cavity via the channel forming device 24, the access cannula 30 and/or an additional delivery tube. The system 20 and related methods of use facilitate formation of the material-receiving cavity (and thus injection of the curable material) at a location laterally displaced from a central axis of the access cannula 30.

The system 20 can be used for a number of different procedures, including, for example, vertebroplasty and other bone augmentation procedures in which curable material is delivered to a site within bone, as well as possibly to remove or aspirate material from a site within bone. The system 20 is highly useful for delivering a curable material in the form of a bone curable material. The phrase "curable material" within the context of the substance that can be delivered by the system 20 of the present disclosure is intended to refer to materials (e.g., composites, polymers, and the like) that have a fluid or flowable state or phase and a hardened, solid or cured state or phase. Curable materials include, but are not limited to, injectable bone cements (such as polymethylmethacrylate (PMMA) bone curable material), which have a flowable state wherein they can be delivered (e.g., injected) by a cannula to a site and subsequently cure to hardened, cured material. Other materials such as calcium phosphates, bone in-growth materials, antibiotics, proteins, etc., can be used in place of, or to augment, bone cement (but do not affect an overriding characteristic of the resultant formulation having a flowable state and a hardened, solid, or cured state). This would allow the body to reabsorb the curable material and/or improve the clinical outcome based on the type of filler implant material.

As mentioned above, the access cannula assembly 22 includes the access cannula 30. The access cannula 30 is provided to be positioned in (or immediately proximate), a target site for delivery of curable material therein. The access cannula 30 can be made of a surgical grade of stainless steel, but may be made of known equivalent materials that are both biocompatible and substantially non-compliant at expected operating pressures. The access cannula 30 defines a proximal portion 40, a distal end 42, and a lumen 44 (hidden in FIG. 1, but shown in FIG. 6A) to allow various equipment, such as the channel forming device 24, the cavity forming device 26, a stylet (not shown), etc., to pass therethrough. In some constructions, the distal end 42 is blunt, but can alternatively be beveled to ease the penetration of the access cannula 30 through the cutaneous and soft tissues, and especially through hard tissues.

Surrounding the proximal portion 40 of the access cannula 30 is an optional handle 46 for manipulating the access cannula 30 and connecting the access cannula 30 with one or more of the devices 24-28. In some constructions, the access cannula assembly 22 further includes a handle connector 48. The handle connector 48 is fluidly connected to the lumen 44, and defines a proximal end 50 of the access cannula 30. Alternatively, the handle connector 48 can incorporate features forming part of a locking mechanism component of the system 20. For example, the handle connector 48 can optionally include a luer-lock type of connector, but other known connecting mechanisms may be successfully interchanged (e.g., a conventional threaded hole, a threaded locking nut arrangement, etc.). Features of the optional locking mechanism are described in U.S. Publication No. 2007/0198024 entitled "Curable Material Delivery Device" and the entire teachings of which are incorporated herein by reference. In other embodiments, the handle 46 and/or the handle connector 48 can be omitted.

The channel forming device 24 is configured to form a channel within bone, and generally includes an elongated shaft 60 distally connected to or forming a distal tip 62. The elongated shaft 60 can be a solid body or a tube. Regardless, the elongated shaft 60 includes a distal segment 64 (referenced generally) defining a pre-set curve or bend 66. As described below, the distal segment 64, and in particular the bend 66, is deflectable, and has a shape memory attribute whereby the distal segment 64 can be forced from the curved shape (shown in FIG. 1) toward a more straightened shape, and will naturally revert back to or toward the curved shape upon removal of the force.

The elongated shaft 60 defines a continuous length between a proximal end 68 and the distal tip 62, with the deflectable distal segment 64, and in particular the bend 66, extending along approximately 10%-50% of a length of the elongated shaft 60 as measured from the distal tip 62. To facilitate formation of a curved channel within a confined bone site (such as with a vertebroplasty procedure), the deflectable distal segment 64 can be formed to define the bend 66 at a predetermined radius of curvature appropriate for the procedure in question. In one construction, the bend 66 is J-shaped (approximating at least a 60° bend). Alternatively, the bend angle can be greater or lesser depending upon the particular procedure for which the channel forming device 24 is to be employed.

To facilitate ready deflection of the deflectable distal segment 64 from the curved shape toward a more straightened state (such as when the elongated shaft 60 is inserted within the access cannula 30) and self-reversion back to or toward the curved shape, the elongated shaft 60, or at least the deflectable distal segment 64, is formed of a shape memory material. In some constructions, the elongated shaft 60, or at least the distal segment 64, comprises Nitinol™, a known shape memory alloy of nickel and titanium. For example, the bend 66 can be formed in the distal segment 64 by deforming a straight wire or tube under extreme heat for a prescribed period of time, which pre-sets a curved shape in the distal segment 64. Alternatively, the pre-set curve or bend 66 can be formed in an initially straight wire or tube by cold working the straight shaft and applying a mechanical stress. Cold working permanently locks a crystalline structure (for example, a partial martensitic crystalline structure) in a portion (i.e., the deflectable distal segment 64) of the shaft, while an unstressed portion remains in, for example, an austenitic structure.

In addition to Nitinol™, other materials exhibiting the above-described shape memory behavior can be employed, including super elastic or pseudoelastic copper alloys, such as alloys of copper, aluminum, and nickel, and alloys of copper, aluminum, and zinc, and alloys of copper and zinc. The deflectable distal segment 64 is formed to be resilient and to naturally assume the desired radius of curvature. In this manner, after the elongated shaft 60, and in particular the deflectable distal segment 64, is flexed or deflected to a substantially straightened shape (not shown), upon subsequent relaxation, the deflectable distal segment 64 "remembers" the pre-set curved shape and relaxes/returns to the bend 66 as described in greater detail below. In yet other embodiments, the curved shape of the distal segment 64 can be effectuated by one or more additional bodies or mechanisms, such as an internal pull wire. Regardless, the elongated shaft 60, including the distal segment 64, is longitudinally rigid such that a distal pushing force applied at or adjacent the proximal end 68 is transferred to the distal tip 62. The longitudinal rigidity of the shaft 60 is such that when the distal tip 62 is in contact with a cancellous bone and the pushing force is sufficient for the distal tip 62 to bore through cancellous bone, the shaft 60 will not longitudinally buckle or collapse.

With embodiments in which the elongated shaft 60 is a tube, one or more side orifices 70 can be provided adjacent the distal tip 62, extending through a thickness of a side wall of the tubular elongated shaft 60. In one construction, a single orifice 70 is provided, and is located "opposite" a direction of the bend 66. In other words, relative to the longitudinal view of FIG. 1, a direction of the bend 66 serves to form the elongated shaft 60 to define an interior bend side 72 and an exterior bend side 74. With these designations in mind, the side orifice 70, where provided, is optionally disposed along the exterior bend side 74. Material (e.g., curable material) can be dispensed from the side orifice(s) 70, and/or material (e.g., bone) can be aspirated into the side orifice(s) 70. In other embodiments, the side orifice(s) 70 can be omitted. In yet other embodiments, the elongated shaft 60 is a solid body or wire.

The distal tip 62 can assume various forms configured to effectuate boring through bone (and in particular cancellous bone). More particularly, in some embodiments, the channel forming device 24 effectuates formation of a channel in cancellous bone by forcibly advancing the distal tip 62 through the bone material. With this technique, the elongated shaft 60 is not rotated or otherwise operated to mechanically cut the bone tissue; instead, the forced advancement of the distal tip 62 compacts and/or or crushes bone material in contact therewith to thereby create a space or channel.

With the above explanation in mind, one construction of the distal tip 62 in accordance with the present disclosure is shown in FIG. 2A. The distal tip 62 has an obround shape, tapering in diameter from an intermediate portion 80 to a leading portion 82. The leading portion 82 terminates at a leading end 84 that can be blunt or sharpened. Regardless, the intermediate portion 80 defines a maximum diameter D of the distal tip 62, with this maximum diameter D being greater than a diameter d of the elongated shaft 60, and in particular along the distal segment 64. However, the maximum diameter D is at least slightly smaller than a diameter of the access cannula lumen 44 (FIG. 6A), such that the channel forming device 44 (FIG. 1), and in particular the distal segment 64 (FIG. 1), can be slidably received through the access cannula 30 (FIG. 1). With the construction of FIG. 2A, a shape of the distal tip 62 is symmetrical relative to a centerline CL defined by the elongated shaft 60.

Figure 2B:
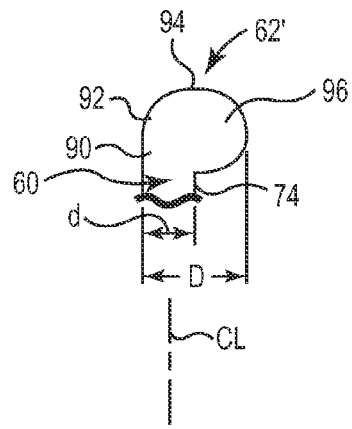
FIG. 2B is a simplified side view of another distal tip useful with the channel forming device of FIG. 1.

Another embodiment distal tip 62' in accordance with principles of the present disclosure is shown in FIG. 2B. The distal tip 62' includes an intermediate portion 90 and a leading portion 92 terminating at a leading end 94. Once again, the leading end 94 can be blunt or sharpened. Further, the intermediate portion 90 defines a maximum diameter D of the distal tip 62' that is greater than the diameter d of the elongated shaft 60, but slightly less than a diameter of the access cannula lumen 44 (FIG. 6A). With the configuration of FIG. 2B, however, a shape of the distal tip 62' is asymmetric relative to the centerline CL of the elongated shaft 60. Effectively, then, the distal tip 62' forms a protrusion or bulge 96 extending from one side of the elongated shaft 60. In some embodiments, the protrusion 96 is defined along the exterior bend side 74 (referenced generally in FIG. 2B and shown in greater detail in FIG. 1). Alternatively, the protrusion 96 can project relative to a different side of the elongated shaft 60.

Figure 2C:
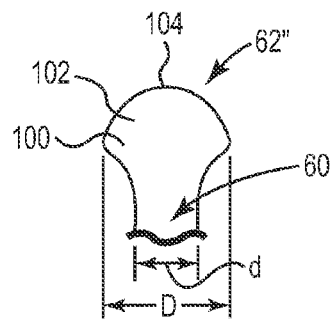
FIG. 2C is a simplified side view of another distal tip useful with the channel forming device of FIG. 1.

Yet another embodiment distal tip 62" in accordance with principles of the present disclosure is shown in FIG. 2C. The distal tip 62" includes an intermediate portion 100 and a leading portion 102 terminating at a leading end 104. The distal tip 62" is akin to the distal tip 62 (FIG. 2A) described above, but presents a more distinct taper to the leading end 104. Once again, the leading end 104 can be blunt or sharpened, and the intermediate portion 100 defines a maximum diameter D that is greater than the diameter d of the elongated shaft 60 yet slightly smaller than the diameter of the access cannula lumen 44 (FIG. 6A).

The distal tips 62-62" (FIGS. 2A-2C) described above represent non-limiting examples in accordance with the present disclosure. In more general terms, the distal tip 62 can have any shape appropriate for boring through cancellous bone when forcibly advanced through the cancellous bone.

Returning to FIG. 1, the channel forming device 24 can optionally include other components, such as a handle 106 attached to the proximal end 68 of the elongated shaft 60. Where provided, the handle 106 facilitates application of a pushing force onto the shaft 60. Further, the handle 106 can include indicia 108 that visually indicates a direction of the bend 66, and the handle 106 can be adapted to interface with the handle connector 48 of the access cannula assembly 22. In other embodiments, the handle 106 is omitted.

The cavity forming device 26 can assume various forms appropriate for forming a void or cavity within bone, and generally includes an elongated body 110 distally connected to or forming a working end 112. The elongated body 110 is sized to be inserted within access cannula lumen 44 (FIG. 6A), and can include one or more tubes, shafts, etc., necessary for operation of the working end 112.

A proximal region 114 of the elongated body 110 is optionally connected to or forms a connector 116. The connector 116 can assume various forms, such as the Y-type connector shown that provides ports fluidly open to various lumen(s) of the elongated body to facilitate operation of the working end 112. Optionally, the connector 116 can include or form features conducive to selective, rigid attachment to the handle connector 48 as described above (e.g., the connector 116 and the handle connector 48 collectively form a locking mechanism). In other embodiments, the connector 116 is omitted.

The working end 112 can include one or more components for forming a cavity or void within bone. For example, in some constructions, the working end 112 includes one or more expandable or inflatable members (e.g., a single balloon, multiple balloons, a single balloon with two or more discernable inflation zones, etc.), constructed to transition between a contracted (e.g., deflated) state in which the working end/balloon 112 can be passed through the access cannula lumen 44 (FIG. 6A), and an expanded (e.g., inflated) state in which the working end/balloon 112 expands and compacts contacted cancellous bone. In this regard, a size and shape of the working end/balloon 112 can be predetermined and/or restrained with one or more additional components (not shown), such as internal and/or external restraints. Regardless, the working end/balloon 112 is structurally robust, able to withstand (e.g., not burst) expected inflation pressures when in contact with cancellous bone.

The cavity forming device 26 can include one or more additional components connected or operable through the proximal region 114 for actuating the working end 112. By way of one non-limiting example, then, the cavity forming device 26 can include a source (not shown) of pressurized fluid (e.g., contrast medium) for inflating the balloon(s) carried or formed by the working end 112. A hand-held syringe-type pump can be used as the pressurized source.

With constructions of the cavity forming device 26 incorporating a balloon(s) as the working end 112, at least a distal region 118 (including the working end/balloon 112 and corresponding portion of the elongated body 110) is relatively flexible, and readily conforms to different shapes (in longitudinal extension) in response to external forces. Thus, while FIG. 1 illustrates the distal region 118 as being relatively linear in longitudinal extension, the distal region 118 will conform to multiple other shapes, such as the shape of a curved channel formed in cancellous bone as described in greater detail below. For example, the elongated body 110 can be a catheter-type, flexible tube forming one (or more) ports that are fluidly open to an interior of the balloon 112. With these embodiments, the catheter body 110 exhibits sufficient longitudinal rigidity to facilitate distal movement of the balloon 112 through a channel, with the distal region 118 following or conforming to a path of the channel.

The material delivery device 28 includes a source 130 of curable material that can assume various forms appropriate for delivering the desired curable material. Typically, the source 130 of curable material comprises a chamber filled with a volume of curable material and employing any suitable injection system or pumping mechanism to transmit curable material out of the chamber. For example, a hand injection system can be used where a user applies force by hand to an injector. The force is translated into pressure on the curable material, forcing the curable material to flow out of the chamber. A motorized system may also be used to apply force.

Tubing 132 is fluidly connected to, and extends from, the source 130 of curable material, and serves as a conduit through which the curable material is delivered. In some embodiments, the tubing 132 is configured for connection to the channel forming device 24, with the channel forming device 24, in turn, being employed to deliver the curable material to the delivery site. In other embodiments, the tubing 132 can be directed through the access cannula 30 to deliver the curable material directly to the delivery site. In yet other embodiments, a separate delivery tool (e.g., a delivery cannula) can be provided, having a deflectable, distal section forming a bend commensurate with the bend 66 of the channel forming device 24 as described above. With these optional embodiments, the delivery cannula is employed to deliver the curable material, via connection to the tubing 132, to the delivery site.

Figure 3A:
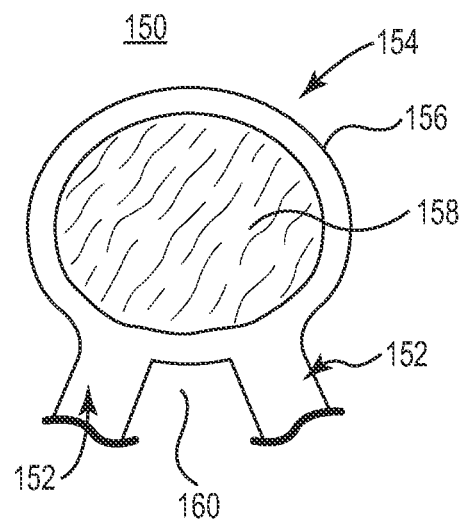
FIG. 3A is a simplified, transverse, sectional view of a vertebra upon which methods in accordance with principles of the present disclosure are useful.
Figure 3B:
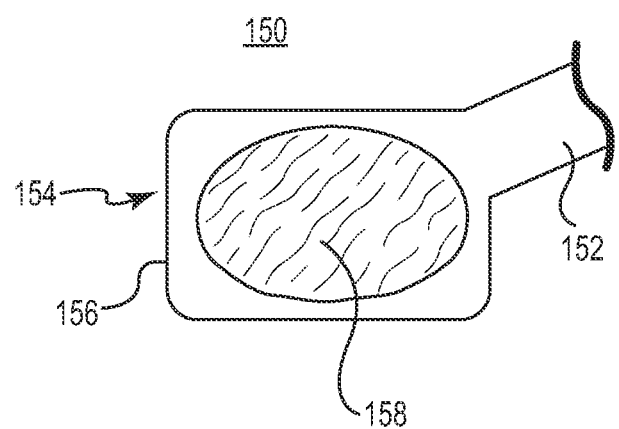
FIG. 3B is a simplified lateral sectional view of the vertebra of FIG. 3A.

Regardless of an exact configuration, systems 20 in accordance with principles of the present disclosure are useful in performing a wide variety of bone stabilizing procedures by injecting or delivering curable material into bone. For example, the systems 20 of the present disclosure can be employed with vertebra-related procedures (e.g., vertebroplasty). To this end, FIGS. 3A and 3B are simplified views of a vertebra 150. As mentioned above, bone stabilization via delivery or injection of curable material has been found to be beneficial in the treatment of defects of the vertebra 150. In general terms, the vertebra 150 includes pedicles 152 and a vertebral body 154 defining a vertebral wall 156 surrounding bodily material 158 (e.g., cancellous bone, blood, marrow, and soft tissue). The pedicles 152 extend from the vertebral body 154 and surround a vertebral foramen 160. As a point of reference, systems and methods of the present disclosure are suitable for accessing a variety of bone sites. Thus, while the vertebra 150 target site is illustrated, it is to be understood that other bone sites can be accessed and treated by systems and methods of the present disclosure (i.e., femur, long bone, rib, sacrum, etc.).

Figure 4A:
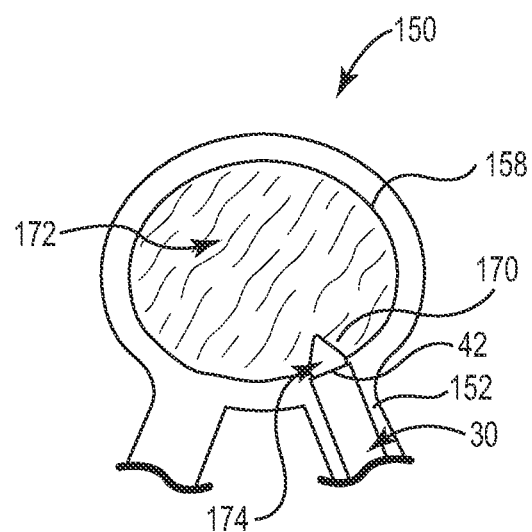
FIGS. 4A-11 illustrate use of cavity formation and curable material delivery systems of the present disclosure in performing a bone stabilization procedure in accordance with principles of the present disclosure.
Figure 4B:
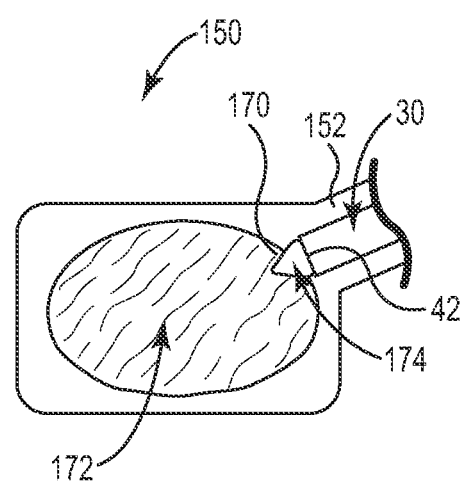
Figure 5A:
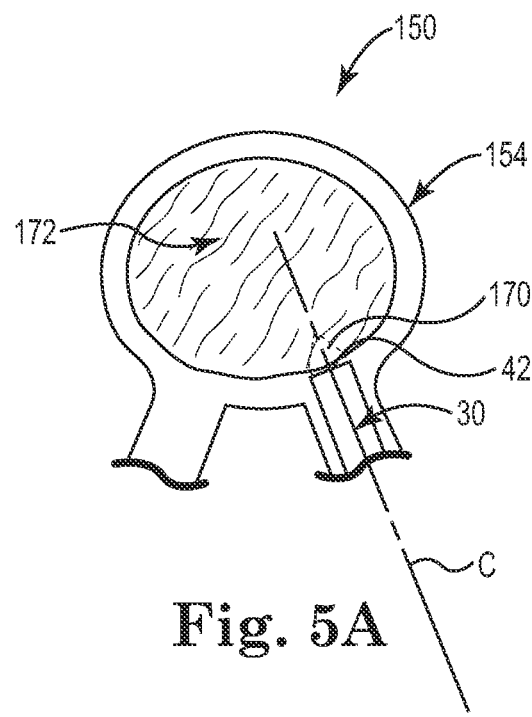
Figure 5B:
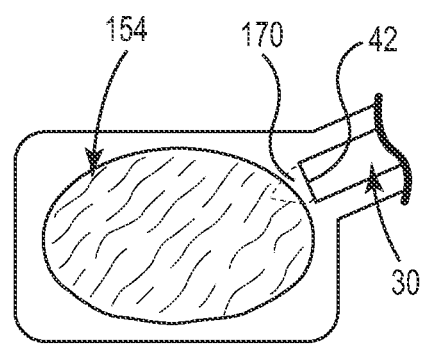

With the anatomy of the vertebra 150 in mind, some methods in accordance with principles of the present disclosure entail the access cannula 30 being initially employed to form an insertion access path 170 generally directed toward to a target site 172 as shown in FIGS. 4A and 4B. In this regard, the insertion access path 170 can be formed through one of the pedicles 152 and into the bodily material 158 adjacent the target site 172. Thus, as illustrated, the access cannula 30 has been driven through the pedicle 152 via a transpedicular approach. The transpedicular approach locates the access cannula 30 between the transverse process and mammillary process of the selected vertebra 150. Alternatively, other approaches toward the target site 172 can be employed (e.g., an anterior approach). In any event, the access cannula 30 provides general access to the target site 172 at the open, distal end 42. As shown, a stylet 174 can be employed to assist in forming the insertion access point or path 170 toward the target site 172. Alternatively, or in addition, the access cannula 30 alone can be configured to sufficiently achieve the insertion access path 170. In yet other embodiments, a separate, outer guide cannula (not shown) can initially be deployed to form the insertion access path 170. Regardless, once positioned, the access cannula 30 can remain relatively stationary relative to the target site 172. Where provided, the stylet 174 is removed from the access cannula 30 resulting in the arrangement of FIGS. 5A and 5B. As shown, the access cannula 30 is retained at the vertebral body 154, with the distal end 42 generally facing the target site 172. However, the intended or desired target site 172 is transversely offset from the access cannula 30. More particularly, and as best reflected in FIG. 5A, a central axis C of the access cannula 30 does not pass directly through the intended target site 172.

Figure 6B:
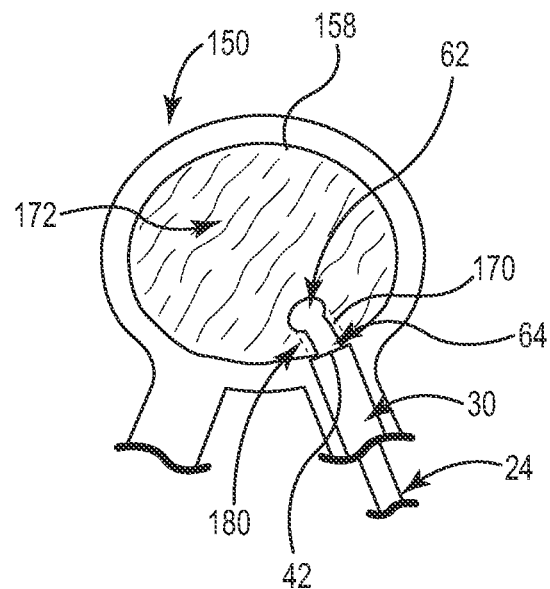
Figure 6C:
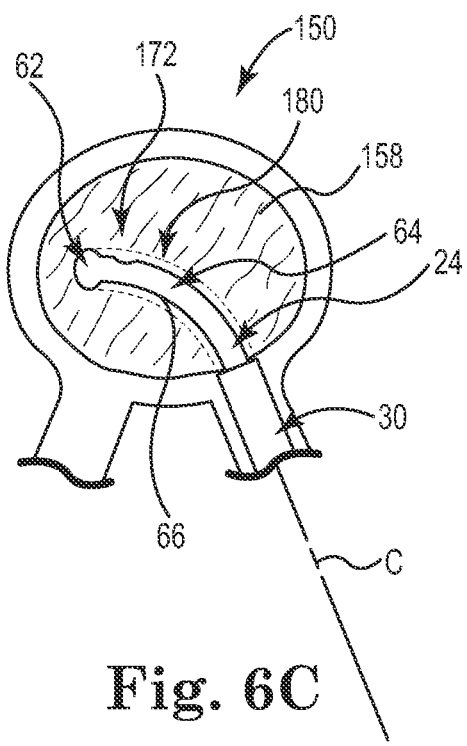

With reference to FIGS. 6A-6C, the channel forming device 24 is deployed through the access cannula 30 to create a curved channel 180 (referenced generally in FIG. 6C) in the cancellous bone (or other bodily material) 158. In particular, the distal segment 64 of the channel forming device 24 is slidably inserted/distally advanced within the access cannula 30. As illustrated generally in FIG. 6A, the distal tip 62 of the channel forming device 24 is poised at the distal end 42 of the access cannula 30. Prior to further distal movement, the distal segment 64, is entirely within the access cannula lumen 44, such that the distal segment 64 is constrained (e.g., deflected or flexed) to a more straightened shape that generally conforms to a shape of the access cannula 30. The force is effectively imparted by the access cannula 30 onto the deflectable distal segment 64 due to the radius of curvature defined by the distal segment 64 in a "natural" state being larger than a diameter of the access cannula lumen 44. This interaction essentially "removes" the pre-set curvature of the bend 66 (FIG. 1), forcing or rendering the deflectable distal segment 64 to a more straightened state (it being understood that because an inner diameter of the access cannula 30 is greater than the diameter d (FIG. 2A) of the elongated shaft 60 as well as slightly greater than the maximum diameter D (FIG. 2A) of the distal tip 62, the distal segment 64 may continue to have a slight curvature within the access cannula 30). Thus, "substantially straightened" is in reference to the elongated shaft 60 being substantially, but not necessarily entirely, linear. Prior to interaction with the cancellous bone material 158, then, the elongated shaft 60 is flexed toward a substantially or more straightened state within the access cannula 30.

The channel forming device 24, and in particular the distal segment 64 is then distally advanced within the access cannula 30, such that at least a portion of the distal segment 64 extends beyond the open distal end 42 of the access cannula 30 and into the cancellous bone 158 immediately adjacent the insertion access path 170 as shown in FIG. 6B. The now unrestrained portion of the distal segment 64 naturally deflects laterally (from the more straightened shape described above) upon exiting the access cannula distal end 42, self-reverting to or toward the pre-set curvature of the bend 66 previously described due to, for example, the shape memory characteristic. In addition, with distal advancement of the distal segment 64, the distal tip 62 intimately contacts and effectively compacts or crushes the cancellous bone 158. Stated otherwise, the area of cancellous bone 158 directly contacted by the advancing distal tip 62 is permanently deformed or compacted, resulting in formation of the channel 180. Taken in combination, then, the channel forming effects of the distal tip 62 and the pre-set curved shape of the distal segment 64 produce or generate the curved channel 180 in response to a distally-directed pushing force applied to the proximal end 68 (FIG. 1) of the channel forming device 24 in a direction generally co-axial with the central axis C of the access cannula 30 as shown in FIG. 6C. The pushing force is translated to the distal tip 62, and is of sufficient magnitude to cause compaction or crushing of the contacted cancellous bone 158. Further, the self-reverting curved shape of the distal segment 64 effectively "directs" the distal tip 62 through a curved or arcuate path while boring through the cancellous bone 158. Advancement of the distal segment 64 continues until the distal tip 62 is located at, or approximately at, the target site 172. Notably, the channel forming device 24 creates the curved channel 180 independent of any naturally occurring "paths" within the cancellous bone 158. For example, the natural anatomy of the cancellous bone (and/or naturally-occurring debris within the vertebral body 154) may tend to inherently direct an otherwise flexible tube (with no pre-set longitudinal curve) toward the target site 172 or away from the target site 172, somewhat like a grown pattern in wood. Under either circumstance, the channel forming device 24 and corresponding methods of use of the present disclosure definitely achieve the curved channel 180 as a direct function of the present curve in the channel forming device 24. Thus, the present disclosure is distinct from a non-linear channel formed by a flexible tube that simply happens to deflect when encountering the natural anatomy.

Figure 7:
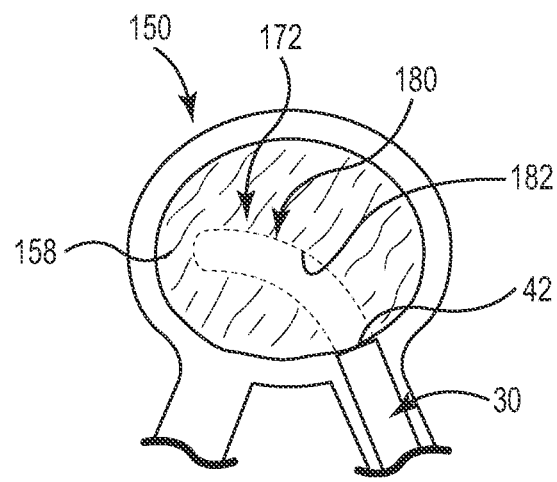

The channel forming device 24 is then removed from the access cannula 30, resulting in the curved channel 180 as shown in FIG. 7. The curved channel 180 is defined through or in the cancellous bone 158, and is fluidly open to the access cannula distal end 42. Due to the compaction caused by the distal tip 62 (FIG. 6C), the cancellous bone 158 "surrounding" the curved channel 180 effectively serves as or provides a discernable perimeter or wall 182.

Figure 8A:
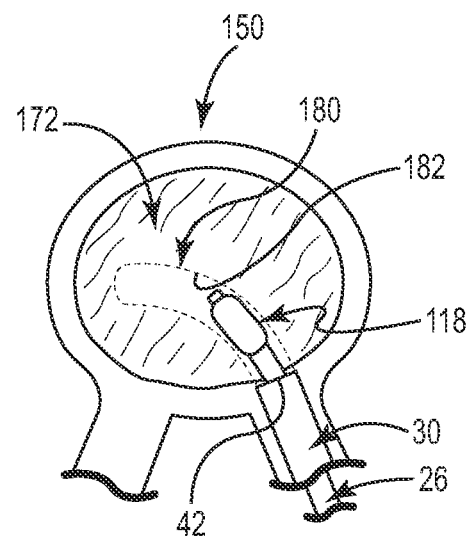
Figure 8B:
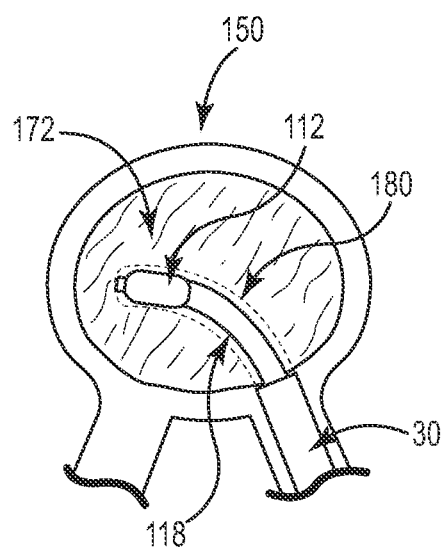

The cavity forming device 26, and in particular the distal region 118, is then inserted through, and distally advanced from, the access cannula 30 as shown in FIG. 8A. In this regard, as portions of the distal region 118 exit the access cannula distal end 42, the distal region 118 follows a path of the curved channel 180. More particularly, the distal region 118 is sufficiently flexible such that upon contacting the channel wall 182 and with further distal advancement, the distal region 118 readily deflects, thereby tracking or following the shape of the curved channel 180. In other words, the distal region 118 follows the path of least resistance, and does not bore through the cancellous bone 158 surrounding the curved channel 180. Distal advancement of the distal region 118 continues through the curved channel 180, resulting in the arrangement of FIG. 8B. In the final location, the working end 112 is at or immediately proximate the target site 172.

Figure 9A:
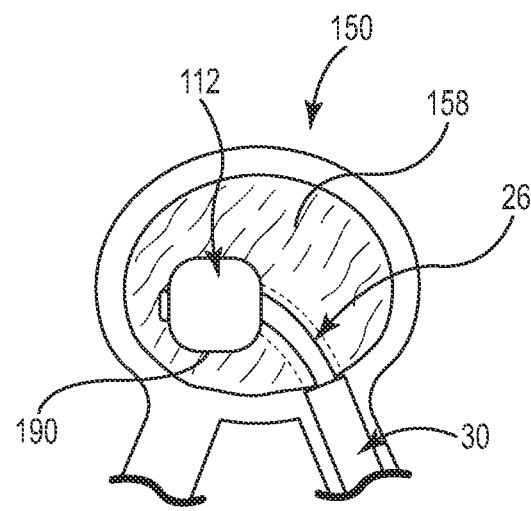
Figure 9B:
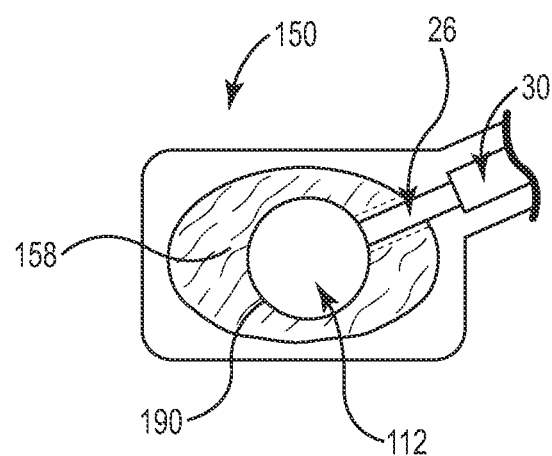
Figure 10A:
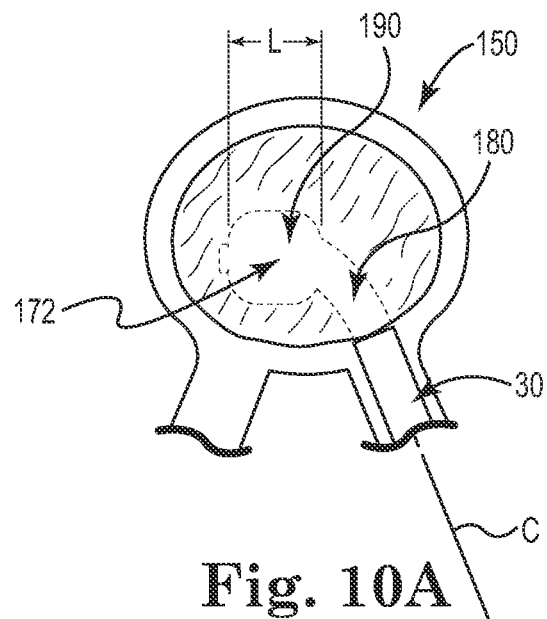
Figure 10B:
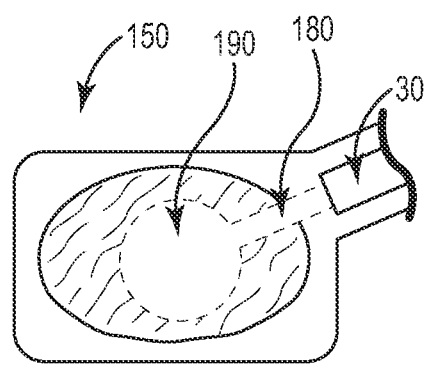

With reference to FIGS. 9A and 9B, the cavity forming device 26 is operated to cause the working end/balloon 112 to form a cavity or void 190 (referenced generally) in the cancellous bone (or other bodily material) 158. For example, the working end/balloon 112 can be expanded (e.g., inflated). The working end/balloon 112 is then transitioned to the contracted state (e.g., deflated), and removed from the access cannula 30. FIGS. 10A and 10B illustrate the cavity 190 in greater detail. As shown, the cavity 190 is fluidly open to the curved channel 180, and thus to the access cannula 30. With specific reference to FIG. 10A, the cavity 190 is formed at the target site 172, but is laterally offset from the central axis C of the access cannula 30. This offset positioning is achieved via the curved shape of the channel 180. A magnitude of the transverse offset is a function of the radius of curvature of the channel 180, as well as an arc length thereof. The cavity 190 can have a variety of different shapes as dictated by a configuration of the working end 112 (FIG. 9A). In some embodiments, the working end 112 can be configured to create the cavity 190 as having a discernable length L. With these optional embodiments, the cavity 190 is spatially oriented such that a direction of the length L is not parallel with the access cannula central axis C.

Figure 11:
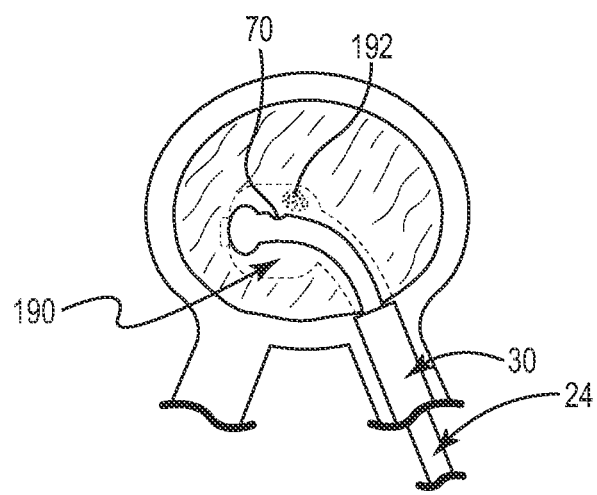

Curable material is subsequently delivered to the cavity 190. For example, in some embodiments and with reference to FIG. 11, the channel forming device 24 is re-introduced through the access cannula 30, and positioned as shown. The source 130 of curable material (FIG. 1) is fluidly connected to the channel forming device 24 and curable material 192 injected or dispensed into the cavity 190 via the side orifice(s) 70. Alternatively, a component apart from the channel forming device 24 can be employed to inject or deliver the curable material 192.

The systems and methods of the present disclosure provide a marked improvement over previous designs. By forming a curved channel within the cancellous bone and through which the cavity forming device is internally located facilitate formation of the cavity at a desired location that is otherwise offset from the central axis of the access cannula.

Although the present disclosure has been described with reference to preferred embodiments, workers skilled in the art will recognize that changes can be made in form and detail without departing from the spirit and scope of the present disclosure.

What is claimed is:

1. A method of injecting curable material to a delivery site within a bone structure, the method comprising:

locating a distal end of an access cannula within the bone structure, the access cannula forming a lumen and defining a central axis; inserting a channel creating device into the lumen;

distally advancing a distal segment of the channel creating device from the distal end and into the bone structure;

creating a curved channel in the bone structure with the distally advancing distal segment, the curved channel defining a curve relative to the central axis; removing the channel creating device;

wherein the distal segment includes a shaft terminating at a distal tip, wherein a maximum outer diameter of the distal tip is greater than an outer diameter of the shaft, and further wherein the step of distally advancing the distal segment includes the distal tip boring through the bone structure;

inserting a distal portion of a cavity creating device into the lumen, the distal portion including an expandable body carried by an elongated body, the expandable body operable between a contracted state and an expanded state;

distally advancing the distal portion from the distal end, including the distal portion following a path of the curved channel; operating the expandable body to form a cavity in the bone structure, the cavity being open to the curved channel; and delivering curable material to the cavity.

2. The method of claim 1, wherein the expandable body is a balloon.

3. The method of claim 2, wherein operating the expandable body to form a cavity includes inflating the balloon.

4. The method of claim 1, wherein the step of the distal portion following a path of the curved channel includes the distal portion deflecting in response to contact with a wall of the curved channel.

5. The method of claim 4, wherein the wall of the curved channel is defined by the bone structure.

6. The method of claim 4, wherein the elongated body of the distal portion is a flexible catheter.

7. The method of claim 1, wherein the distal segment of the channel creating device has a shape memory characteristic and naturally assumes a curved shape in longitudinal extension.

8. The method of claim 7, wherein the step of inserting the distal segment into the lumen includes the access cannula forcing the distal segment to deflect from the curved shape toward a straightened shape.

9. The method of claim 7, wherein the step of distally advancing the distal segment includes at least a portion of the distal segment distal the distal end of the access cannula naturally reverting toward the curved shape.

10. The method of claim 1, wherein the maximum outer diameter of the distal tip is less than a diameter of the access cannula lumen.

11. The method of claim 1, wherein the distal tip is sharpened.

12. The method of claim 1, wherein the distal tip is asymmetric relative to a centerline of the shaft.

13. The method of claim 1, wherein the shaft is tubular and forms at least one port adjacent the tip, the further wherein the step of delivering curable material includes reintroducing the channel creating device into the access cannula and delivering the curable material through the at least one port.

14. The method of claim 1, wherein the curved channel has a diameter commensurate with a maximum diameter of the distal tip, and further wherein the cavity is defined by a maximum dimension greater than the curved channel diameter.

15. The method of claim 1, wherein the bone structure is a vertebrae.

16. The method of claim 1, wherein the bone structure includes an outer wall surrounding cancellous bone, and further wherein the curved channel is created in the cancellous bone independent of any naturally-occurring pathways in the cancellous bone.

* * * * *